US011110152B2

(12) United States Patent
Ledford et al.

(10) Patent No.: US 11,110,152 B2
(45) Date of Patent: Sep. 7, 2021

(54) COMPOSITIONS AND METHODS FOR TREATING AND PREVENTING LUNG DISEASE

(71) Applicant: ARIZONA BOARD OF REGENTS ON BEHALF OF THE UNIVERSITY OF ARIZONA, Tucson, AZ (US)

(72) Inventors: Julie Ledford, Tucson, AZ (US); Monica Kraft, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 16/093,063

(22) PCT Filed: Apr. 11, 2017

(86) PCT No.: PCT/US2017/026889
§ 371 (c)(1),
(2) Date: Oct. 11, 2018

(87) PCT Pub. No.: WO2017/180546
PCT Pub. Date: Oct. 19, 2017

(65) Prior Publication Data
US 2019/0117741 A1   Apr. 25, 2019

Related U.S. Application Data

(60) Provisional application No. 62/320,950, filed on Apr. 11, 2016.

(51) Int. Cl.
*A61K 38/17* (2006.01)
*A61K 9/00* (2006.01)
*A61P 11/06* (2006.01)

(52) U.S. Cl.
CPC ............ *A61K 38/395* (2013.01); *A61K 9/008* (2013.01); *A61P 11/06* (2018.01)

(58) Field of Classification Search
None
See application file for complete search history.

(56) References Cited

U.S. PATENT DOCUMENTS

| 8,623,832 | B2 * | 1/2014 | Awasthi | C07K 14/78 514/21.3 |
|---|---|---|---|---|
| 2007/0129297 | A1 * | 6/2007 | Cochrane | A61K 9/0082 514/1.7 |
| 2014/0256613 | A1 | 9/2014 | Awasthi | |

OTHER PUBLICATIONS

AAA36520.1 (https://www.ncbi.nlm.nih.gov/protein/AAA36520 Apr. 27, 1993).*
Q9N1X3_PIG; https://www.uniprot.org/uniprot/Q9N1X3 Oct. 1, 2000.*
Mosen et al. (J Allergy Clin cimmunol 2008:122:507-511).*
EMedicine (<https://www.emedicinehealth.com/chronic_obstructive_pulmonary_disease_copd/article_em.htm#copd_facts>2018).*
Merck Manual (https://www.merckmanuals.com/professional/pulmonary-disorders/chronic-obstructive-pulmonary-disease-and-related-disorders/chronic-obstructive-pulmonary-disease-copd>2018).*
Bousquet et al. The public health implications of asthma. Bull World Health Organ. 2005;83(7):548-54.
Mannino et al. Surveillance for asthma—United States, 1980-1999. MMWR Surveill Summ. 2002;51(1):1-13.
Halwani R, et al. Airway remodeling in asthma. Curr Opin Pharmacol. 2010;10(3):236-45.
Firszt R, Kraft M. Pharmacotherapy of severe asthma. Curr Opin Pharmacol. 2010;10(3):266-71.
Kim HY et al. The many paths to asthma: phenotype shaped by innate and adaptive immunity. Nat Immunol. 2010;11(7):577-84.
Peat JK, Woolcock AJ, Cullen K. Rate of decline of lung function in subjects with asthma. Eur J Respir Dis. 1987;70(3):171-9.
Osborne ML, Pedula KL, O'Hollaren M, Ettinger KM, Stibolt T, Buist AS, et al. Assessing future need for acute care in adult asthmatics: the Profile of Asthma Risk Study: a prospective health maintenance organization-based study. Chest. 2007;132(4):1151-61.
Dougherty RH, Fahy JV. Acute exacerbations of asthma: epidemiology, biology and the exacerbation-prone phenotype. Clin Exp Allergy. 2009;39(2):193-202.
Han S, Mallampalli RK. The role of surfactant in lung disease and host defense against pulmonary infections. Annals of the American Thoracic Society. 2015;12(5):765-74. Epub Mar. 6, 2015 doi: 10.1513/AnnalsATS.201411-507FR.
Wenzel, S.E., Nature medicine, 2012. 18(5): p. 716-25.
Green, R.N., et al., Lancet, 2002. 360(9347): p. 1715-21.
Duncan, C.J., et al., The European respiratory journal, 2003. 22(3): p. 484-90.
Gibson, P.G., et al., Thorax, 2003. 58(2): p. 116-21.
Leitch, A.E., et al., Relevance of granulocyte apoptosis to resolution of inflammation at the respiratory mucosa. Mucosal immunology, 2008. 1(5): p. 350-63.
Wenzel, S.E., et al., American journal of respiratory and critical care medicine, 1999. 160(3): p. 1001-8.
Jayaram, L., et al., The European respiratory journal, 2006. 27(3): p. 483-94.
Fitzpatrick, A.M., et al., The Journal of allergy and clinical immunology, 2008. 121(6): p. 1372-8, 1378 e1-3.
Choudhry, S., et al., Pharmacogenetics and genomics, 2010. 20(6): p. 351-8.
Nielson, C.P. and N.E. Hadjokas, American journal of respiratory and critical care medicine, 1998. 157(1): p. 184-91.

* cited by examiner

*Primary Examiner* — James H Alstrum-Acevedo
*Assistant Examiner* — Tara L Martinez
(74) *Attorney, Agent, or Firm* — Casimir Jones, S.C.; Robert A. Goetz

(57) ABSTRACT

Provided herein are compositions and methods for treating and preventing lung disease. In particular, provided herein are SP-A peptides and uses thereof in the treatment and prevention of lung disease (e.g., asthma or COPD).

4 Claims, 7 Drawing Sheets
Specification includes a Sequence Listing.

COMPOSITIONS AND METHODS FOR TREATING AND PREVENTING LUNG DISEASE

CROSS-REFERENCE TO RELATED APPLICATIONS

The present application is a U.S. 371 national phase entry of International Patent Application No. PCT/US2017/026889, filed Apr. 11, 2017, which claims priority to and the benefit of U.S. Provisional Patent Application No. 62/320,950, filed Apr. 11, 2016 which is hereby incorporated by reference in their entireties.

STATEMENT REGARDING FEDERALLY SPONSORED RESEARCH OR DEVELOPMENT

This invention was made with government support under Grant Nos. R01 HL125602 and P01 AI081672 awarded by NIH. The government has certain rights in the invention.

FIELD OF THE INVENTION

Provided herein are compositions and methods for treating and preventing lung disease. In particular, provided herein are SP-A peptides and uses thereof in the treatment and prevention of lung disease (e.g., asthma or COPD).

BACKGROUND OF THE INVENTION

Asthma is the most common respiratory disease in both children and adults, and presents as a syndrome of non-specific airways hyperresponsiveness, inflammation and intermittent respiratory symptoms affecting 10% of the population (Bousquet et al. Bull World Health Organ. 2005; 83(7):548-54. PubMed PMID: 16175830; Mannino et al. Surveillance for asthma—United States, 1980-1999. MMWR Surveill Summ. 2002; 51(1):1-13. PubMed PMID: 12420904). It is triggered by infection, environmental allergens or other stimuli (Bousquet et al. Bull World Health Organ. 2005; 83(7):548-54. PubMed PMID: 16175830; Mannino et al. Surveillance for asthma—United States, 1980-1999. MMWR Surveill Summ. 2002; 51(1):1-13. PubMed PMID: 12420904).

Asthma remains poorly understood and difficult to manage in many cases due to the heterogeneity of the disease. A significant cause of morbidity and mortality in asthma is the acute exacerbation, which can lead to airway injury, remodeling, lung function decline and death. (Halwani R, et al. Curr Opin Pharmacol. 2010; 10(3):236-45. PubMed PMID: 20591736; Firszt R, Kraft M. Pharmacotherapy of severe asthma. Curr Opin Pharmacol. 2010; 10(3):266-71. PubMed PMID: 20462794). Most exacerbations are caused by respiratory infection such as rhinovirus or *Mycoplasma pneumoniae*. The response to infection is complex, involving both the innate and adaptive immune system (Kim H Y et al. The many paths to asthma: phenotype shaped by innate and adaptive immunity. Nat Immunol. 2010; 11(7):577-84. PubMed PMID: 20562844). Exacerbations in more severe asthmatics are of particular concern, as hospitalizations for acute exacerbations account for one-third of the $14.7 billion dollars spent annually on asthma-related health care in the US. In addition, exacerbations in this population are associated with accelerated lung function decline (Peat J K, Woolcock A J, Cullen K. Rate of decline of lung function in subjects with asthma. Eur J Respir Dis. 1987; 70(3):171-9. PubMed PMID: 3569449; Peat J K, Woolcock A J, Cullen K. Rate of decline of lung function in subjects with asthma. Eur J Respir Dis. 1987; 70(3):171-9. PubMed PMID: 3569449). As reduced lung function is a risk factor for severe exacerbation (Osborne M L, Pedula K L, O'Hollaren M, Ettinger K M, Stibolt T, Buist A S, et al. Assessing future need for acute care in adult asthmatics: the Profile of Asthma Risk Study: a prospective health maintenance organization-based study. Chest. 2007; 132(4):1151-61. PubMed PMID: 17573515; Dougherty R H, Fahy J V. Acute exacerbations of asthma: epidemiology, biology and the exacerbation-prone phenotype. Clin Exp Allergy. 2009; 39(2):193-202. PubMed PMID: 19187331), this vicious cycle can promote an exacerbation-prone phenotype of asthma. Thus, an understanding of the mechanisms driving asthma exacerbations has been a critical barrier to progress in the understanding of asthma pathobiology.

Intact immune system and host defense functions are critical to preventing exacerbations of asthma. Surfactant is a lipoprotein complex that reduces surface tension at the air-liquid interface of the lung and participates in host defense (Han S, Mallampalli R K. The role of surfactant in lung disease and host defense against pulmonary infections. Annals of the American Thoracic Society. 2015; 12(5):765-74. Epub 2015/03/06. doi: 10.1513/AnnalsATS.201411-507FR. PubMed PMID: 25742123). The pulmonary surfactant system of the lung is an extracellular lipid and protein complex, present at the air/tissue interface, which regulates both the biophysical properties of the alveolar compartment, and the innate immune system of the organ. It has been shown that surfactant protein A (SP-A) promotes key cellular functions that can attenuate the severity of the disease and the exacerbation, which includes enhancing apoptosis of eosinophils, a critical cell in asthma pathobiology, reduce mucin production by airway epithelial cells in the setting of interleukin (IL)-13 exposure, a cytokine essential to the allergic asthma phenotype and reduces IL-6 production, another cytokine important in type 2 or allergic inflammation.

Airway inflammation is a hallmark feature of asthma. Eosinophils are prominent in individuals with a type 2 inflammatory asthma phenotype, and accrue in large numbers in the circulation, sputum, and airway mucosa (see, e.g., Wenzel, S. E., Nature medicine, 2012. 18(5): p. 716-25). Eosinophil accumulation and prolonged viability in the airways is strongly correlated with greater asthma severity (see, e.g., Green, R. H., et al., Lancet, 2002. 360(9347): p. 1715-21; Duncan, C. J., et al., The European respiratory journal, 2003. 22(3): p. 484-90; Gibson, P. G., et al., Thorax, 2003. 58(2): p. 116-21; Leitch, A. E., et al., Mucosal immunology, 2008. 1(5): p. 350-63) and their presence is driven by the type 2 cytokines interleukin (IL)-4, 5 and 13. Recent studies have shown that within the group of severe asthmatics, approximately 50% have eosinophils present in their lung tissues (see, e.g., Wenzel, S. E., et al., American journal of respiratory and critical care medicine, 1999. 160(3): p. 1001-8; Wenzel, S. E., Asthma phenotypes: the evolution from clinical to molecular approaches. Nature medicine, 2012. 18(5): p. 716-25). Moreover, treatment strategies targeted at reducing eosinophils have been shown to reduce asthma admission rates and exacerbations (see, e.g., Green, R. H., et al., Lancet, 2002. 360(9347): p. 1715-21; Jayaram, L., et al., The European respiratory journal, 2006. 27(3): p. 483-94). Clearance and rapid removal of apoptotic cells is an important process leading to the resolution of inflammation and mitigation of asthma symptoms. Inefficient apoptotic cell clearance results in secondary necrosis or cytolysis, the release of cellular contents that can damage tissue, and prolong inflammation and duration of asthma symptoms. Additionally, asthma severity is strongly correlated with prolonged eosinophil viability (see, e.g., Duncan, C. J., et al., The European respiratory journal, 2003. 22(3): p. 484-90; Fitzpatrick, A. M., et al., The Journal of allergy and clinical immunology, 2008. 121(6): p. 1372-8, 1378 e1-3; Leitch, A. E., et al., Relevance of granulocyte apoptosis to resolution of inflammation at the respiratory mucosa. Mucosal immunology, 2008. 1(5): p. 350-63). Interestingly, inhaled beta-2 agonists, which are the mainstay of asthma treatment worldwide, have been shown to prolong eosinophil survival ((see, e.g., Nielson, C. P. and N. E. Hadjokas, American journal of respiratory and critical care medicine, 1998. 157(1): p. 184-91) and may actually exacerbate asthma or at least contribute to the variable response seen with beta-2 agonists (see, e.g., Choudhry, S., et al., Pharmacogenetics and genomics, 2010. 20(6): p. 351-8).

Additional treatments for asthma are needed.

SUMMARY OF THE INVENTION

Surfactant protein-A (SP-A) is a secreted lipoprotein complex that is known to modulate host responses to infectious and environmental insults. Allelic variants of the two human SP-A genes, SP-A1 and SP-A2, have been linked to more severe forms of several diseases, including susceptibility to idiopathic pulmonary fibrosis, infant RSV infection and *Aspergillus*-mediated allergies.

Experiments described herein demonstrated that, in asthma patients, the SP-A2 Gln223Lys (223Q/K within the SP-A wild type amino acid sequence shown at SEQ ID NO: 1) allele is associated with decreased lung function, decreased asthma control, and increased BAL and serum eosinophilia. The studies demonstrated that SP-A is a key regulator of eosinophil degranulation and survival, and may thereby significantly influence asthma severity. Using in vitro studies with isolated eosinophils, SP-A deficient mice, and SP-A oligomers containing the specific SP-A allele of interest, it was found that SP-A directly stimulates eosinophil apoptosis, that this effect can be recapitulated by specific SP-A peptides, and that SP-A allelic variants differentially modulate eosinophil responses.

```
Human Wild Type amino acid sequence for SP-A
                                          (SEQ ID NO: 1)
         10          20          30          40
MWLCPLALNL  ILMAASGAAC  EVKDVCVGSP  GIPGTPGSHG 50          60          70          80
LPGRDGRDGV  KGDPGPPGPM  GPPGETPCPP  GNNGLPGAPG 90         100         110         120
VPGERGEKGE  AGERGPPGLP  AHLDEELQAT  LHDFRHQILQ 130         140         150         160
TRGALSLQGS  IMTVGEKVFS  SNGQSITFDA  IQEACARAGG 170         180         190         200
RIAVPRNPEE  NEAIASFVKK  YNTYAYVGLT  EGPSPGDFRY 210         220         230         240
SDGTPVNYTN  WYRGEPAGRG  KEQCVEMYTD  GQWNDRNCLY

SRLTICEF
```

Based on data described herein from an allergic model in mice, it is contemplated that SP-A encounters eosinophils in the bronchoalveolar compartment and is a critical regulator of their apoptosis during the resolution phase of inflammatory processes. The data shows that SP-A plays a role in directly inducing apoptosis signaling pathways in eosinophils, which results in attenuation of allergic phenotypes such as mucin production and eosinophilia. It was also shown that SP-A attenuates mucin induced by IL-13 in airway epithelial cells obtained from asthmatic subjects with allergic or type 2 asthma.

Accordingly, the present invention provides compositions and methods for treating and preventing lung disease. In particular, provided herein are SP-A peptides and uses thereof in the treatment and prevention of lung disease (e.g., asthma).

For example, in some embodiments, a composition comprising a peptide comprising an amino acid sequence selected from, for example, PAGRGKEQCV (SEQ ID NO: 2), EMYTDGQWND (SEQ ID NO: 3), KEQCVEMYTD (SEQ ID NO: 4), PAGRGKEKCV (SEQ ID NO: 5), KEKCVEMYTD (SEQ ID NO: 6), PAGRGKEKCVE-MYTDGQWND (SEQ ID NO: 7), PAGRGKEQCVE-MYTDGQWND (SEQ ID NO: 8) or peptides with at least 90% (e.g., 91%, 92%, 93%, 94%, 95%, 96%, 97%, 98%, 99%, or 100%) identity to the peptides is provided. Further embodiments provide a composition consisting essentially of a peptide selected from, for example, PAGRGKEQCV (SEQ ID NO: 2), EMYTDGQWND (SEQ ID NO: 3), KEQCVEMYTD (SEQ ID NO: 4), PAGRGKEKCV (SEQ ID NO: 5), KEKCVEMYTD (SEQ ID NO: 6), PAGRGKEKCVEMYTDGQWND (SEQ ID NO: 7), PAGRGKEQCVEMYTDGQWND (SEQ ID NO: 8). In some embodiments, the composition is a pharmaceutical composition. In some embodiments, the composition comprises a pharmaceutically acceptable carrier. In some embodiments, the composition is formulated for pulmonary delivery.

Further embodiments provide a system, comprising: a) any one of the compositions described herein; and b) a device for pulmonary delivery of the composition. In some embodiments, the device is a metered dose inhaler.

Additional embodiments provide a method of enhancing SP-A activity in a cell, comprising: delivering any one of the compositions described herein to a cell. In some embodiments, the cell is a lung cell. In some embodiments, the cell is in vivo. In some embodiments, the composition reduces mucin production and/or reduces eosinophilia in the lung. In some embodiments, the cell is in a subject diagnosed with asthma. In some embodiments, the administering decreases or prevents symptoms or markers of asthma in the subject. In some embodiments, subject is obese or is not obese. In some embodiments, the peptide binds to a receptor selected from, for example FC (CD16/32), Sirp-alpha, TLR-2, or EGFR.

Still other embodiments provide a method of treating or preventing a lung disease (e.g., asthma or COPD) in a subject, comprising: administering any one of the compositions described herein to the subject.

Yet other embodiments provide the use of any one of the compositions described herein to enhance SP-A activity in a cell. Other embodiments provide the use of any one of the compositions described herein to treat or prevent lung disease (e.g., asthma or COPD) in a subject.

Additional embodiments are described herein.

DEFINITIONS

Figure 1A:
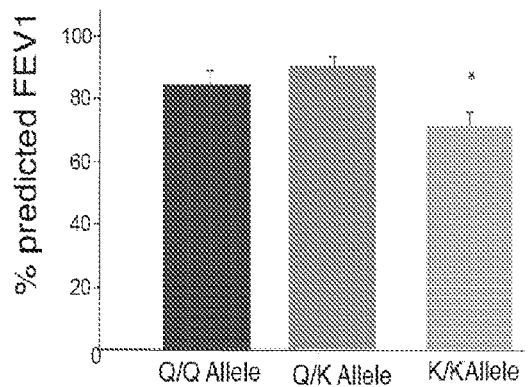
FIG. 1A-B. Genetic variation in SP-A2 is associated with changes in lung function and asthma control. The percent predicted FEV1 and asthma control questionnaire score in a cohort of 53 asthmatic subjects stratified by alleles of rs1965708 (Gln$^{223}$Lys) of the SP-A2 gene. The asthmatic subjects with the 223K/K genotype demonstrate significantly worse asthma control (right panel) and lower lung function (left panel) as compared to the heterozygotes for 223Q/K and major allele (homozygosity for 223Q/Q) genotype. *p<0.05 compared to Q/Q.

The terms "polypeptide" and "protein" are used interchangeably to refer to a polymer of amino acid residues, comprising natural or non-natural amino acid residues, and are not limited to a minimum length. Thus, peptides, oligopeptides, dimers, multimers, and the like are included within the definition. Both full-length proteins and fragments thereof are encompassed by the definition. The terms also include post-translational modifications of the polypeptide, including, for example, glycosylation, sialylation, acetylation, and phosphorylation. Furthermore, a "polypeptide" herein also refers to a modified protein such as single or multiple amino acid residue deletions, additions, and substitutions to the native sequence, as long as the protein maintains a desired activity. For example, a serine residue may be substituted to eliminate a single reactive cysteine or to remove disulfide bonding or a conservative amino acid substitution may be made to eliminate a cleavage site. These modifications may be deliberate, as through site-directed mutagenesis, or may be accidental, such as through mutations of hosts, which produce the proteins or errors due to polymerase chain reaction (PCR) amplification.

As used herein, the term "peptide" refers a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (synthetic) sequence.

"Wildtype" refers to a non-mutated version of a gene, allele, genotype, polypeptide, or phenotype, or a fragment of any of these. It may occur in nature or be produced recombinantly.

A "variant" is a nucleic acid molecule or polypeptide that differs from a referent nucleic acid molecule or polypeptide by single or multiple amino acid substitutions, deletions, and/or additions and substantially retains at least one biological activity of the referent nucleic acid molecule or polypeptide.

The terms "peptide mimetic" or "peptidomimetic" refer to a peptide-like molecule that emulates a sequence derived from a protein or peptide. A peptide mimetic or peptidomimetic may contain amino acids and/or non-amino acid components. Examples of peptidomimitecs include chemically modified peptides, peptoids (side chains are appended to the nitrogen atom of the peptide backbone, rather than to the α-carbons), β-peptides (amino group bonded to the β carbon rather than the α carbon), etc.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:
  1) Alanine (A) and Glycine (G);
  2) Aspartic acid (D) and Glutamic acid (E);
  3) Asparagine (N) and Glutamine (Q);
  4) Arginine (R) and Lysine (K);
  5) Isoleucine (I), Leucine (L), Methionine (M), and Valine (V);
  6) Phenylalanine (F), Tyrosine (Y), and Tryptophan (W);
  7) Serine (S) and Threonine (T); and
  8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

"Subject," "individual," "host," "animal," and "patient" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

As used herein, the terms "administration" and "administering" refer to the act of giving a drug, prodrug, or other agent, or therapeutic treatment (e.g., SP-A peptide) to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., multiple SP-A peptides or an SP-A peptide and another therapeutic agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

"Treatment," as used herein, covers any administration or application of a therapeutic for disease in a mammal, including a human, and includes inhibiting the disease, arresting its development, or relieving the disease, for example, by causing regression, or restoring or repairing a lost, missing, or defective function; or stimulating an inefficient process.

A "pharmaceutically acceptable carrier" refers to a non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

DETAILED DESCRIPTION OF THE INVENTION

As noted, experiments described herein demonstrated that, in asthma patients, the SP-A2 Gln223Lys (223Q/K) allele is associated with decreased lung function, decreased asthma control, and increased BAL and serum eosinophilia. The studies demonstrated that SP-A is a key regulator of eosinophil degranulation and survival, mucin secretion and type 2 inflammation, and may thereby significantly influence asthma severity. Using in vitro studies with isolated eosinophils, SP-A deficient mice, and SP-A oligomers containing the specific SP-A allele of interest, it was found that SP-A directly stimulates eosinophil apoptosis, that this effect can be recapitulated by specific SP-A peptides, and that SP-A allelic variants differentially modulate eosinophil responses.

Based on data described herein from an allergic model in mice, it is contemplated that SP-A encounters eosinophils in the bronchoalveolar compartment and is a critical regulator of their apoptosis during the resolution phase of inflammatory processes. The data shows that SP-A plays a role in directly inducing apoptosis signaling pathways in eosinophils, which results in attenuation of allergic phenotypes such as mucin production and eosinophilia. It was also shown that SP-A attenuates mucin and IL-6 induced by IL-13 in airway epithelial cells obtained from asthmatic subjects with allergic or type 2 asthma.

Accordingly, provided herein are compositions and methods for treating and preventing lung disease. In particular, provided herein are SP-A peptides and uses thereof in the treatment and prevention of lung disease (e.g., asthma).

In certain embodiments, the present invention provides a treatment for asthma using peptides whose sequence is derived from the active region of endogenous human SP-A that contains the major Q allele at position 223 of the SP-A2 peptide. For example, in some embodiments, a composition comprising a peptide comprising, consisting essentially of, or consisting of an amino acid sequence selected from, for example, PAGRGKEQCV (SEQ ID NO: 2), EMYTDGQWND (SEQ ID NO: 3), KEQCVEMYTD (SEQ ID NO: 4), PAGRGKEKCV (SEQ ID NO: 5), KEKCVEMYTD (SEQ ID NO: 6), PAGRGKEKCVEMYTDGQWND (SEQ ID NO: 7), PAGRGKEQCVEMYTDGQWND (SEQ ID NO: 8), or peptides with at least 90% (e.g., 91%, 92%, 93%, 94%, 95%, 96%, 97%, 98%, 99%, or 100%) identity to the peptides is provided. Further embodiments provide a composition consisting essentially of a peptide selected from, for example, PAGRGKEQCV (SEQ ID NO: 2), EMYTDGQWND (SEQ ID NO: 3), KEQCVEMYTD (SEQ ID NO: 4), PAGRGKEKCV (SEQ ID NO: 5), KEKCVEMYTD (SEQ ID NO: 6), PAGRGKEKCVEMYTDGQWND (SEQ ID NO: 7), PAGRGKEQCVEMYTDGQWND (SEQ ID NO: 8). In some embodiments, the peptide binds to a receptor selected from, for example FC (CD16/32), Sirp-alpha, TLR-2, or EGFR.

The present invention further provides variants and mimetics of the SP-A peptides described herein. In some embodiments, an SP-A peptide comprises conservative, semi-conservative, and/or non-conservative substitutions relative to the peptides described herein (e.g., at positions involved in SP-A signaling or positions not involved in SP-A signaling).

Embodiments are not limited to specific substitutions. In some embodiments, the peptides described herein are further modified (e.g., substitution, deletion, or addition of standard amino acids; chemical modification; etc.). Modifications that are understood in the field include N-terminal modification, C-terminal modification (which protects the peptide from proteolytic degradation), alkylation of amide groups, hydrocarbon "stapling" (e.g., to stabilize alpha-helix conformations). In some embodiments, the peptides described herein may be modified by conservative residue substitutions, for example, of the charged residues (K to R, R to K, D to E and E to D). In some embodiments, such conservative substitutions provide subtle changes, for example, to the receptor binding sites with the goal of improving specificity and/or biological activity. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled peptide chemist. The α-carbon of an amino acid may be mono- or dimethylated.

In some embodiments, one or more intra-peptide disulfide bonds are introduced (e.g., between two cysteines within the peptide. In some embodiments, the presence of an intra-peptide disulfide bond stabilizes the peptide.

In some embodiments, any embodiments described herein may comprise peptidomimetics corresponding to the peptides described herein with various modifications that are understood in the field. In some embodiments, residues in the peptide sequences described herein may be substituted with amino acids having similar characteristics (e.g., hydrophobic to hydrophobic, neutral to neutral, etc.) or having other desired characteristics (e.g., more acidic, more hydrophobic, less bulky, more bulky, etc.). In some embodiments, non-natural amino acids (or naturally-occurring amino acids other than the standard 20 amino acids) are substituted in order to achieve desired properties.

In some embodiments, residues having a side chain that is positively charged under physiological conditions, or residues where a positively-charged side chain is desired, are substituted with a residue including, but not limited to: lysine, homolysine, δ-hydroxylysine, homoarginine, 2,4-diaminobutyric acid, 3-homoarginine, D-arginine, arginal (—COOH in arginine is replaced by —CHO), 2-amino-3-guanidinopropionic acid, nitroarginine (N(G)-nitroarginine), nitrosoarginine (N(G)-nitrosoarginine), methylarginine (N-methylarginine), ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexinic acid, p-aminobenzoic acid and 3-aminotyrosine and, histidine, 1-methylhistidine, and 3-methylhistidine.

A neutral residue is a residue having a side chain that is uncharged under physiological conditions. A polar residue preferably has at least one polar group in the side chain. In some embodiments, polar groups are selected from hydroxyl, sulfhydryl, amine, amide and ester groups or other groups which permit the formation of hydrogen bridges.

In some embodiments, residues having a side chain that is neutral/polar under physiological conditions, or residues where a neutral side chain is desired, are substituted with a residue including, but not limited to: asparagine, cysteine, glutamine, serine, threonine, tyrosine, citrulline, N-methylserine, homoserine, allo-threonine and 3,5-dinitro-tyrosine, and (3-homoserine.

Residues having a non-polar, hydrophobic side chain are residues that are uncharged under physiological conditions, preferably with a hydropathy index above 0, particularly above 3. In some embodiments, non-polar, hydrophobic side chains are selected from alkyl, alkylene, alkoxy, alkenoxy, alkylsulfanyl and alkenylsulfanyl residues having from 1 to 10, preferably from 2 to 6, carbon atoms, or aryl residues having from 5 to 12 carbon atoms. In some embodiments, residues having a non-polar, hydrophobic side chain are, or residues where a non-polar, hydrophobic side chain is desired, are substituted with a residue including, but not limited to: leucine, isoleucine, valine, methionine, alanine, phenylalanine, N-methylleucine, tert-butylglycine, octylglycine, cyclohexylalanine, β-alanine, 1-aminocyclohexylcarboxylic acid, N-methylisoleucine, norleucine, norvaline, and N-methylvaline.

In some embodiments, peptide and polypeptides are isolated and/or purified (or substantially isolated and/or substantially purified). Accordingly, in such embodiments, peptides and/or polypeptides are provided in substantially isolated form. In some embodiments, peptides and/or polypeptides are isolated from other peptides and/or polypeptides as a result of solid phase peptide synthesis, for example. Alternatively, peptides and/or polypeptides can be substantially isolated from other proteins after cell lysis from recombinant production. Standard methods of protein purification (e.g., HPLC) can be employed to substantially purify peptides and/or polypeptides. In some embodiments, the present invention provides a preparation of peptides and/or polypeptides in a number of formulations, depending on the desired use. For example, where the polypeptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc. In some embodiments, peptides and/or polypeptides are prepared in lyophilized form. Moreover, such preparations can include other desired agents, such as small molecules or other peptides, polypeptides or proteins. Indeed, such a preparation comprising a mixture of different embodiments of the peptides and/or polypeptides described here may be provided.

In some embodiments, provided herein are peptidomimetic versions of the peptide sequences described herein or variants thereof. In some embodiments, a peptidomimetic is characterized by an entity that retains the polarity (or non-polarity, hydrophobicity, etc.), three-dimensional size, and functionality (bioactivity) of its peptide equivalent but wherein all or a portion of the peptide bonds have been replaced (e.g., by more stable linkages). In some embodiments, 'stable' refers to being more resistant to chemical degradation or enzymatic degradation by hydrolytic enzymes. In some embodiments, the bond which replaces the amide bond (e.g., amide bond surrogate) conserves some properties of the amide bond (e.g., conformation, steric bulk, electrostatic character, capacity for hydrogen bonding, etc.). Chapter 14 of "Drug Design and Development", Krogsgaard, Larsen, Liljefors and Madsen (Eds) 1996, Horwood Acad. Publishers provides a general discussion of techniques for the design and synthesis of peptidomimetics and is herein incorporated by reference in its entirety. Suitable amide bond surrogates include, but are not limited to: N-alkylation (Schmidt, R. et al., Int. J. Peptide Protein Res., 1995, 46,47; herein incorporated by reference in its entirety), retro-inverse amide (Chorev, M. and Goodman, M., Acc. Chem. Res, 1993, 26, 266; herein incorporated by reference in its entirety), thioamide (Sherman D. B. and Spatola, A. F. J. Am. Chem. Soc., 1990, 112, 433; herein incorporated by reference in its entirety), thioester, phosphonate, ketomethylene (Hoffman, R. V. and Kim, H. O. J. Org. Chem., 1995, 60, 5107; herein incorporated by reference in its entirety), hydroxymethylene, fluorovinyl (Allmendinger, T. et al., Tetrahydron Lett., 1990, 31, 7297; herein incorporated by reference in its entirety), vinyl, methyleneamino (Sasaki, Y and Abe, J. Chem. Pharm. Bull. 1997 45, 13; herein incorporated by reference in its entirety), methylenethio (Spatola, A. F., Methods Neurosci, 1993, 13, 19; herein incorporated by reference in its entirety), alkane (Lavielle, S. et. al., Int. J. Peptide Protein Res., 1993, 42, 270; herein incorporated by reference in its entirety) and sulfonamido (Luisi, G. et al. Tetrahedron Lett. 1993, 34, 2391; herein incorporated by reference in its entirety).

As well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Suitable peptidomimetics include reduced peptides where the amide bond has been reduced to a methylene amine by treatment with a reducing agent (e.g. borane or a hydride reagent such as lithium aluminum-hydride); such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142; herein incorporated by reference in its entirety.

Any carrier which can supply an active peptide or polypeptide (e.g., without destroying the peptide or polypeptide within the carrier) is a suitable carrier, and such carriers are well known in the art. In some embodiments, compositions are formulated for administration by any suitable route, including but not limited to, orally (e.g., such as in the form of tablets, capsules, granules or powders), sublingually, buccally, parenterally (such as by subcutaneous, intravenous, intramuscular, intradermal, or intrasternal injection or infusion (e.g., as sterile injectable aqueous or non-aqueous solutions or suspensions, etc.)), nasally (including administration to the nasal membranes, such as by inhalation spray), topically (such as in the form of a cream or ointment), transdermally (such as by transdermal patch), rectally (such as in the form of suppositories), etc.

A pharmaceutical composition may be administered in the form, which is formulated with a pharmaceutically acceptable carrier and optional excipients, adjuvants, etc. in accordance with good pharmaceutical practice. The peptide-based pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. pill, injection, etc.), the composition form is determined. In general, it is preferred to use a unit dosage form in order to achieve an easy and accurate administration of the active pharmaceutical peptide or polypeptide. In general, the therapeutically effective pharmaceutical compound is present in such a dosage form at a concentration level ranging from about 0.5% to about 99% by weight of the total composition, e.g., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. In some embodiments, an peptides-based pharmaceutical composition is provided in a unit dosage form for administration to a subject, comprising a peptides or polypeptide and one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

The peptides and the polypeptides encompassing a substantially alpha helical peptide region that are disclosed herein may be further derivatized by chemical alterations, such as amidation, glycosylation, acylation, sulfation, phosphorylation, acetylation, and cyclization. Such chemical alterations can be imparted through chemical or biochemical methodologies, as well as through in vivo processes, or any combination thereof.

The peptides and polypeptides described herein may be prepared as salts with various inorganic and organic acids and bases. Such salts include salts prepared with organic and inorganic acids, for example, with HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, alkali earth salts, e.g. calcium and magnesium salts, and zinc salts. The salts may be formed by conventional means, such as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The peptides and polypeptides described herein can be formulated as pharmaceutically acceptable salts and/or complexes thereof. Pharmaceutically acceptable salts include acid addition salts such as those containing sulfate, hydrochloride, phosphate, sulfamate, acetate, citrate, lactate, tartrate, succinate, oxalate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The peptides and polypeptides described herein may be formulated as pharmaceutical compositions for use in conjunction with the methods of the present disclosure. Compositions disclosed herein may conveniently be provided in the form of formulations suitable for parenteral administration, including subcutaneous, intramuscular and intravenous administration, nasal administration, pulmonary administration, or oral administration. Suitable formulation of peptides and polypeptides for each such route of administration is described in standard formulation treatises, e.g., Remington's Pharmaceutical Sciences by E. W. Martin. See also Wang, Y. J. and Hanson, M. A. "Parenteral Formulations of Proteins and Peptides: Stability and Stabilizers," Journal of Parenteral Science and Technology, Technical Report No. 10, Supp. 42:2S (1988).

Certain of the peptides and polypeptides described herein may be substantially insoluble in water and sparingly soluble in most pharmaceutically acceptable protic solvents and in vegetable oils. In certain embodiments, cyclodextrins may be added as aqueous solubility enhancers. Cyclodextrins include methyl, dimethyl, hydroxypropyl, hydroxyethyl, glucosyl, maltosyl and maltotriosyl derivatives of alpha-, beta-, and gamma-cyclodextrin. An exemplary cyclodextrin solubility enhancer is hydroxypropyl-beta-cyclodextrin (HPBCD), which may be added to any of the above-described compositions to further improve the aqueous solubility characteristics of the peptides or polypeptides. In one embodiment, the composition comprises 0.1% to 20% HPBCD, 1% to 15% HPBCD, or from 2.5% to 10% HPBCD. The amount of solubility enhancer employed will depend on the amount of peptide or polypeptide of the present disclosure in the composition. In certain embodiments, the peptides may be formulated in non-aqueous polar aprotic solvents such as DMSO, dimethylformamide (DMF) or N-methylpyrrolidone (NMP).

In some cases, it will be convenient to provide the peptide or polypeptide and another active agent in a single composition or solution for administration together. In other cases, it may be more advantageous to administer the additional agent separately from said polypeptide. For use, pharmaceutical compositions of the peptides and polypeptides described herein may be provided in unit dosage form containing an amount of the peptide or polypeptide effective for a single administration. Unit dosage forms useful for subcutaneous administration include prefilled syringes and injectors.

In certain embodiments, the polypeptide is administered in an amount, expressed as a daily equivalent dose regardless of dosing frequency, of 50 micrograms ("mcg") per day, 60 mcg per day, 70 mcg per day, 75 mcg per day, 100 mcg per day, 150 mcg per day, 200 mcg per day, or 250 mcg per day. In some embodiments, the polypeptide is administered in an amount of 500 mcg per day, 750 mcg per day, or 1 milligram ("mg") per day. In yet further embodiments, the polypeptide is administered in an amount, expressed as a daily equivalent dose regardless of dosing frequency, of 1-10 mg per day, including 1 mg per day, 1.5 mg per day, 1.75 mg per day, 2 mg per day, 2.5 mg per day, 3 mg per day, 3.5 mg per day, 4 mg per day, 4.5 mg per day, 5 mg per day, 5.5 mg per day, 6 mg per day, 6.5 mg per day, 7 mg per day, 7.5 mg per day, 8 mg per day, 8.5 mg per day, 9 mg per day, 9.5 mg per day, or 10 mg per day. In various embodiments, the polypeptide is administered on a monthly dosage schedule. In other embodiments, the polypeptide is administered biweekly. In yet other embodiments, the polypeptide is administered weekly. In certain embodiments, the polypeptide is administered daily ("QD"). In select embodiments, the polypeptide is administered twice a day ("BID"). In typical embodiments, the polypeptide is administered for at least 3 months, at least 6 months, at least 12 months, or more. In some embodiments, the polypeptide is administered for at least 18 months, 2 years, 3 years, or more.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 .mu.m. Suitable nebulizer devices are provided commercially, for example, by PARI GmbH (Starnberg, German). Other nebulizer devices include Respimat (Boehringer Ingelheim) and those disclosed, for example, in U.S. Pat. No. 6,123,068 to Lloyd et al. and WO 97/12687 (Eicher et al.).

A representative pharmaceutical composition for use in a nebulizer inhaler comprises an isotonic aqueous solution comprising a SP-A peptide or a pharmaceutically acceptable salt or solvate or stereoisomer thereof.

In another specific embodiment of this invention, the pharmaceutical composition comprising the active agent is administered by inhalation using a dry powder inhaler. Such dry powder inhalers typically administer the active agent as a free-flowing powder that is dispersed in a patient's airstream during inspiration. In order to achieve a free flowing powder, the active agent is typically formulated with a suitable excipient such as lactose or starch.

A representative pharmaceutical composition for use in a dry powder inhaler comprises dry lactose having a particle size between about 1 .mu.m and about 100 .mu.m and micronized particles of SP-A peptide, or a pharmaceutically acceptable salt or solvate or stereoisomer thereof.

Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237 to Newell et al.); Diskus (GlaxoSmithKline) (see, e.g., U.S. Pat. No. 6,378,519 to Davies et al.); Turbuhaler (AstraZeneca, Wilmington, Del.) (see, e.g., U.S. Pat. No. 4,524,769 to Wetterlin); Rotahaler (GlaxoSmithKline) (see, e.g., U.S. Pat. No. 4,353,365 to Hallworth et al.) and Handihaler (Boehringer Ingelheim). Further examples of suitable DPI devices are described in U.S. Pat. No. 5,415,162 to Casper et al., U.S. Pat. No. 5,239,993 to Evans, and U.S. Pat. No. 5,715,810 to Armstrong et al., and references cited therein.

In yet another specific embodiment of this invention, the pharmaceutical composition comprising the active agent is administered by inhalation using a metered-dose inhaler. Such metered-dose inhalers typically discharge a measured amount of the active agent or a pharmaceutically acceptable salt or solvate or stereoisomer thereof using compressed propellant gas. Accordingly, pharmaceutical compositions administered using a metered-dose inhaler typically comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company).

A representative pharmaceutical composition for use in a metered-dose inhaler comprises from about 0.01% to about 5% by weight of a compound of SP-A peptide, or a pharmaceutically acceptable salt or solvate or stereoisomer thereof; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are provided in U.S. Pat. No. 6,006,745 to Marecki and U.S. Pat. No. 6,143,277 to Ashurst et al. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.).

For additional examples of processes of preparing respirable particles, and formulations and devices suitable for inhalation dosing see U.S. Pat. No. 6,268,533 to Gao et al., U.S. Pat. No. 5,983,956 to Trofast, U.S. Pat. No. 5,874,063 to Briggner et al., and U.S. Pat. No. 6,221,398 to Jakupovic et al.; and WO 99/55319 (Glaxo Group Ltd.) and WO 00/30614 (AstraZeneca AB).

In some embodiments, peptides/polypeptides are provided in pharmaceutical compositions and/or co-administered (concurrently or in series) with one or more additional therapeutic agents. Such additional agents may be for treatment or prevention of lung inflammation (e.g., asthma). Additional agents may include, but are not limited to: Short-acting beta2-adrenoceptor agonists (SABA), such as salbutamol (albuterol USAN); anticholinergic medications, such as ipratropium bromide, inhaled epinephrine, inhaled or systemic corticosteroids; leukotriene receptor antagonists (e.g., montelukast and zafirlukast); and combinations thereof.

In some embodiments, provided herein are methods for treating patients suffering from (or at risk of) lung disease (e.g., asthma) and/or in need of treatment (or preventative therapy). In some embodiments, subjects are obese or are not obese. In some embodiments, subjects are identified as having an SP-A genotype associated with increased risk of asthma or severe asthma (e.g., those genotypes described herein).

In some embodiments, a pharmaceutical composition comprising at least one SP-A peptide or polypeptide described herein is delivered to such a patient in an amount and at a location sufficient to treat the condition. In some embodiments, peptides and/or polypeptides (or pharmaceutical composition comprising such) can be delivered to the patient systemically or locally, and it will be within the ordinary skill of the medical professional treating such patient to ascertain the most appropriate delivery route, time course, and dosage for treatment. It will be appreciated that application methods of treating a patient most preferably substantially alleviates or even eliminates such symptoms; however, as with many medical treatments, application of the inventive method is deemed successful if, during, following, or otherwise as a result of the inventive method, the symptoms of the disease or disorder in the patient subside to an ascertainable degree.

The present disclosure is not limited to the treatment of asthma. Any inflammatory conditions known in the art or otherwise contemplated herein may be treated in accordance with the presently disclosed and claimed inventive concept(s). Non-limiting examples of disease conditions having inflammation associated therewith include infection-related or non-infectious inflammatory conditions in the lung (e.g., asthma, sepsis, chronic obstructive pulmonary disease (COPD), lung infections, Respiratory Distress Syndrome, bronchopulmonary dysplasia, etc.); infection-related or non-infectious inflammatory conditions in other organs (e.g., colitis, Inflammatory Bowel Disease, diabetic nephropathy, hemorrhagic shock); inflammation-induced cancer (i.e., cancer progression in patients with colitis or Inflammatory Bowel Disease); and the like.

EXPERIMENTAL

Example 1

Figure 1B:
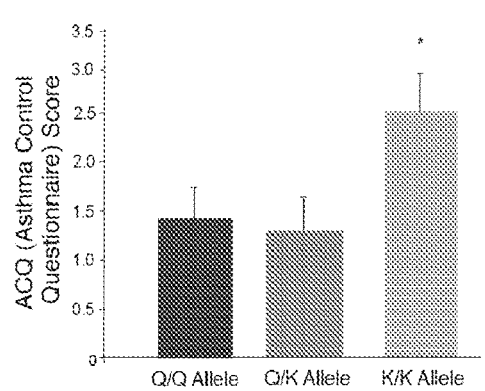

This example demonstrates that a SP-A genotype at position 223 affects lung function and asthma control. Previous studies have shown that SP-A derived from asthmatic subjects is dysfunctional in regulating inflammatory conditions, such as IL-8 and MUCSAC production (see, e.g., Wang, Y., et al., Journal of immunology, 2012. 188(7): p. 3371-81). To then determine if the SP-A genotype influences lung function, lung physiology and asthma control was genotyped and measured in 53 mild-moderate asthmatics not on controller therapy. As shown in FIG. 1A, of the 53 asthmatics screened, those that are homozygous for the minor allele (SP-A2 K223K) have worse lung function (FEV1%) than those subjects with the Q223Q or Q223K genotype. Moreover, this cohort of asthmatic subjects demonstrate worse asthma control (asthma control questionnaire; ACQ) than asthmatics with the AC or CC genotype (FIG. 1B).

Figure 2A:
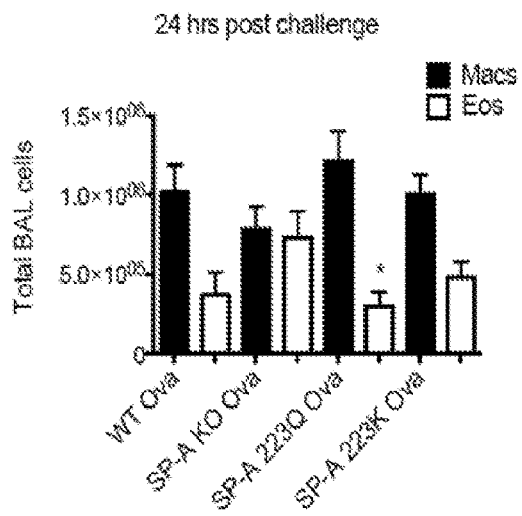
FIG. 2A-B. Analysis of inflammation in SP-A2 humanized mice in the Ova model. Mice were sensitized and challenged in the Ova model and BAL cellularity (left panel) was assessed 24 hrs post challenge and mucin production (right panel) was assessed 7 days post challenge. Presence of human SP-A 223Q in mice resulted in more protection as determined by less eosinophilia and mucin production as compared to SP-A$^{-/-}$ mice. SP-A 223Q expressing mice had similar BAL eosinophilia and mucin production as compared to WT control mice (that have normal mouse SP-A) after Ova challenge.
Figure 2B:
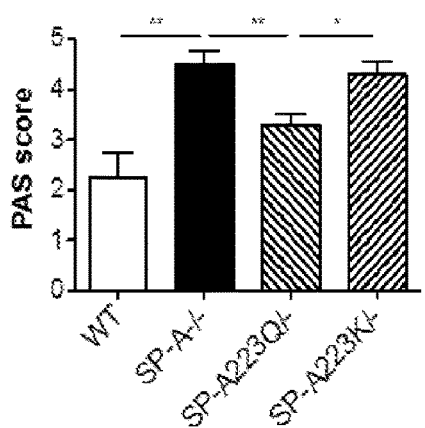

Experiments further demonstrated that SP-A humanized mice exhibit different phenotypes in an allergic model. In order to study more mechanistically the effect of genetic variation in SP-A at position 223Q/K in asthma, SP-A humanized mice that express either the SP-A223Q (major allele) or SP-A223K (minor allele) were generated. It was discovered that when challenged in the Ova model of allergic airways disease the SP-A223Q allele confers more protection as compared to the SP-A223K allele. As shown below in FIG. 2A, SP-A223Q mice have significantly decreased eosinophilia as compared to mice deficient in SP-A 24 hrs post challenge and they also have significantly reduced mucin production (PAS scores) 7 days post challenge (FIG. 2B).

Figure 3A:
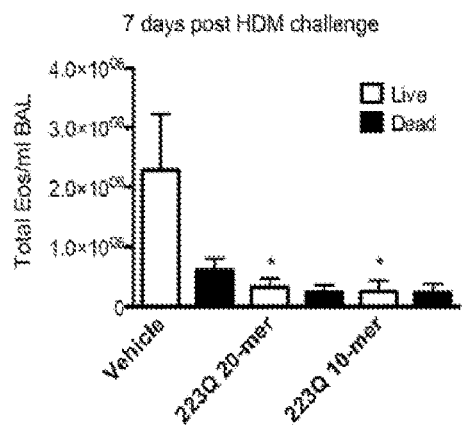
FIG. 3A-B. Analysis of inflammation in mice that receive "therapeutic" SP-A peptides in the HDM model. Mice were sensitized and challenged in the HDM model according to common methods. Twenty-four hours after the last challenge, mice received either vehicle, a 20-mer or a 10-mer that encompassed the active site containing 223Q. BAL cellularity (left panel) and mucin production (right panel) were assessed 7 days post challenge to assess the role of SP-A on allergic airways resolution. SP-A KO mice have significantly enhanced BAL eosinophilia as compared to WT mice. Both 223Q and 223K mice are somewhat protected in the acute phase of this model.
Figure 3B:
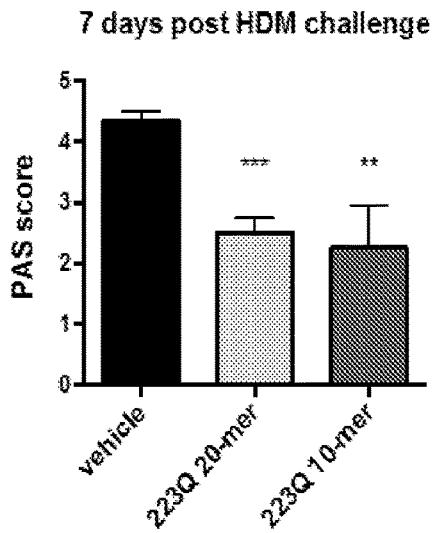

Experiments further demonstrated that SP-A peptides that encompass the 223Q active site attenuate airway eosinophils and mucin production in an allergic model. Since asthmatic subjects harboring the 223K (minor) allele had worse asthma control and lung function as compared to individuals with the 223Q (major) allele and since similar findings were observed in the SP-A humanized mice in an allergic model, experiments were performed to find the active region of SP-A. It was determined that the active peptide is a 10 AA peptide that includes the 223Q site and is located in the carbohydrate recognition domain of endogenous SP-A. As shown in FIGS. 3A and 3B, SP-A deficient mice were challenged in the HDM model and 24 hrs after the last challenge, either a 20AA SP-A (PAGRGKEQCVEMYTDGQWND (SEQ ID NO: 8)) or a 10AA SP-A (KEQCVEMYTD (SEQ ID NO: 4)) was given and compared to those mice receiving vehicle treatment. Those mice receiving the SP-A peptides had significantly less eosinophilia in the lavage compartment (FIG. 3A) and less mucin production (FIG. 3B) as compared to vehicle treated mice.

Figure 4:
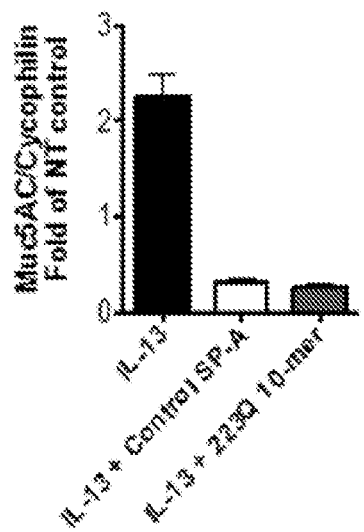
FIG. 4. SP-A 223Q 10-mer peptides significantly suppress MUCSAC expression following IL-13 exposure in human cells. Airway epithelial cells at ALI from two asthmatic subjects exposed to IL-13 alone, and IL-13 plus SP-A2 peptide that include the Gln at position 223 in the lectin domain (223Q). Full-length oligomeric SP-A that is homozygous at position 223Q/Q was used as a positive control. After 48 hours incubation, MUCSAC expression was determined by RT-PCR.

Experiments further demonstrated that SP-A peptide (10AA) that encompass the 223Q active site attenuate phenotypes in primary human airway epithelial cells from asthmatics. Experiments were conducted wherein airway epithelial cells from two subjects with asthma not on controller therapy were cultured at air liquid interface for two weeks. In separate conditions the cells were exposed to each peptide at 50 ng/ml for 30 minutes followed by IL-13 at 50 ng/ml and incubated for 48 hours. Cells were placed in Trizol MUCSAC was determined by RT-PCR. FIG. 4 shows a dramatic reduction in MUCSAC expression with each of the peptides to the level of negative control. The 10 AA length is especially useful as a therapeutic agent as its size renders it able to be packaged into an inhaler type of device for delivery to the airways. This experiment demonstrates that the 223Q peptide has efficacy in suppressing mucin gene expression in human airway epithelial cells in the setting of IL-13 exposure.

In summary, these experiments demonstrated that SP-A genotype at position 223 affects lung function and asthma control; SP-A humanized mice exhibit different phenotypes in an allergic model dependent on position 223Q/K, SP-A peptides that encompass the 223Q active site attenuate phenotypes in an allergic model, SP-A peptide (10AA) that encompasses the 223Q active site attenuates Muc5AC in primary human airway epithelial cells from asthmatics.

Further results are shown in FIGS. 5-9.

Figure 5:
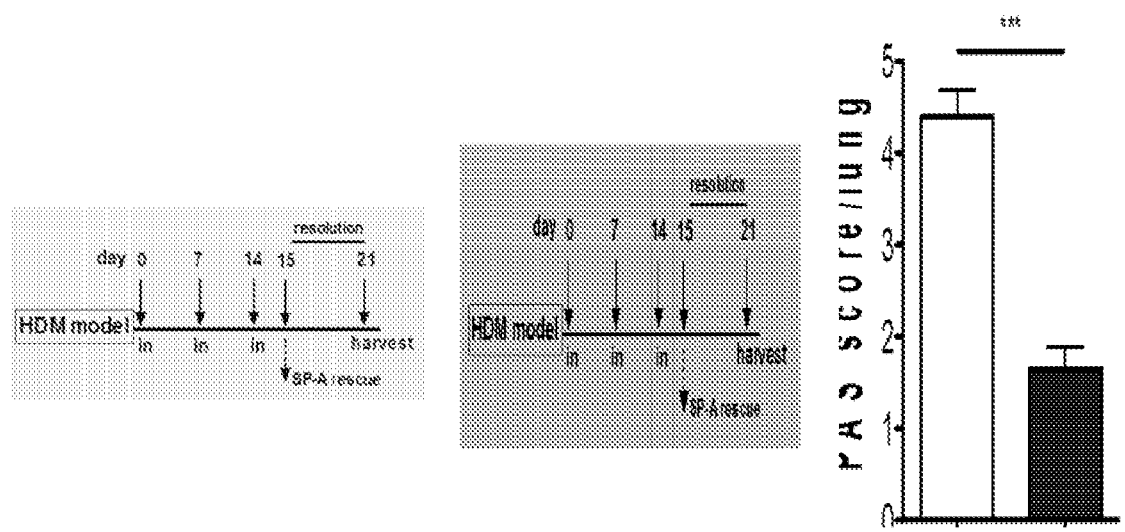
FIG. 5. SP-A 223Q peptide can reduce mucin production in allergic model.

Regarding FIG. 5, WT C57BL/6 mice were sensitized and challenged in the house dust mite (HDM) model according to standard methods on days 0, 7, 14 (black arrows). Twenty-four hours after the last challenge, mice received either scrambled vehicle or a 20-mer SP-A peptide (dotted arrow) that encompassed the active site containing 223Q (at a physiologic dose of 25 µg/mouse delivered in 40 µl of sterile saline) by oropharyngeal instillation. Lung histological sections were analyzed for mucin production as assessed by PAS stain/scoring to determine if the SP-A peptide could protect from HDM-induced airway mucin production. Similar protective effects were observed on days 5 and 7 after SP-A peptide treatment. Peptide sequence: PAGRGKEQCVEMYTDGQWND (SEQ ID NO: 8).

Figure 6:
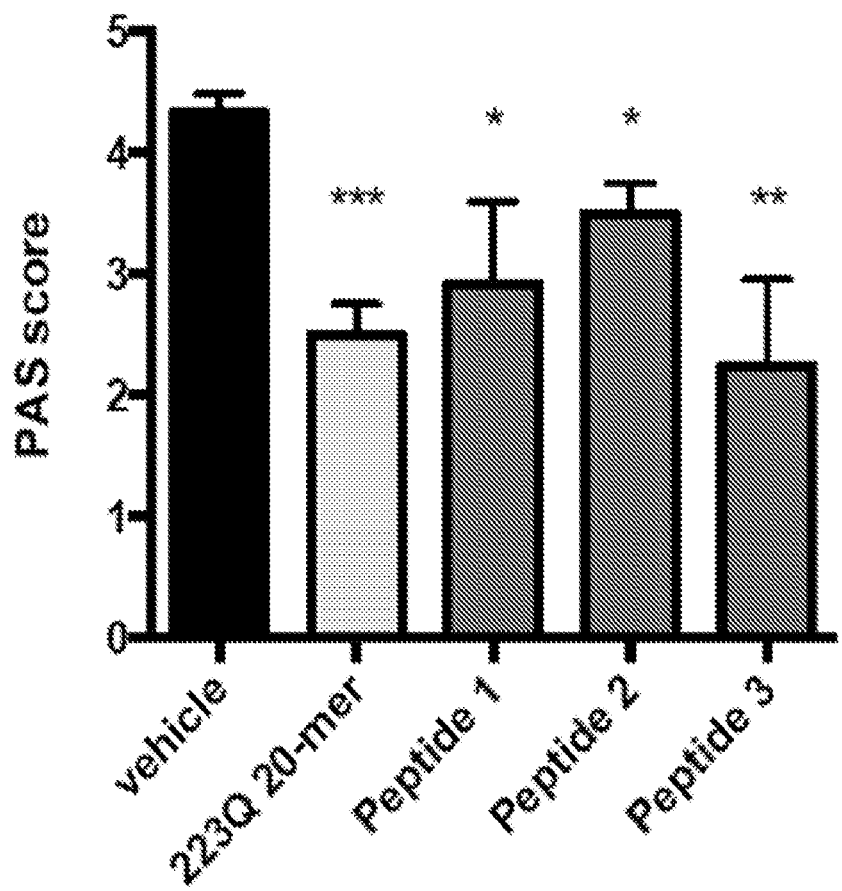
FIG. 6. Shortened 10AA peptides reduce mucin production in mouse HDM model.

Regarding FIG. 6, WT C57BL/6 mice were sensitized and challenged in the house dust mite (HDM) model according to standard methods on days 0, 7, 14 as shown in FIG. 5 (black arrows). Twenty-four hours after the last challenge, mice received either scrambled vehicle, 20-mer, or 10-mer SP-A peptides (dotted arrow) that encompassed the active site containing 223Q (at a physiologic dose of 25 µg/mouse delivered in 40 µl of sterile saline) by oropharyngeal instillation. Lung histological sections were analyzed for mucin production as assessed by PAS stain/scoring to determine if the SP-A peptide could protect from HDM-induced airway mucin production. Similar protective effects were observed on days 5 and 7 after SP-A peptide treatment. Peptide sequences: 20-mer PAGRGKEQCVEMYTDGQWND (SEQ ID NO: 8), peptide 1 PAGRGKEQCV (SEQ ID NO: 2), peptide 2 EMYTDGQWND (SEQ ID NO: 3), peptide 3 KEQCVEMYTD (SEQ ID NO: 4).

Figure 7:
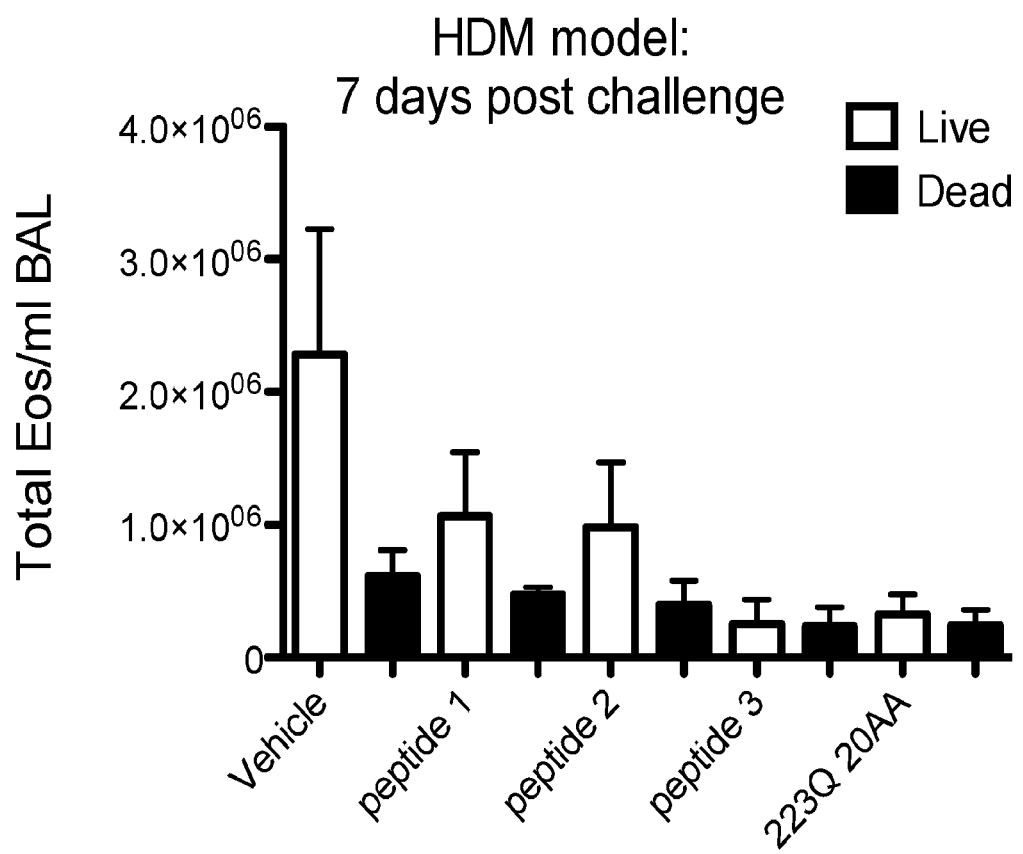
FIG. 7. Shortened 10AA peptides reduce eosinophilia in mouse HDM model.

Regarding FIG. 7, WT C57BL/6 mice were sensitized and challenged in the house dust mite (HDM) model according to standard methods on days 0, 7, 14 as shown in FIG. 5 (black arrows). Twenty-four hours after the last challenge, mice received either scrambled vehicle, 20-mer, or 10-mer SP-A peptides (dotted arrow) that encompassed the active site containing 223Q (at a physiologic dose of 25 µg/mouse delivered in 40 µl of sterile saline) by oropharyngeal instillation. Bronchoalveolar lavage samples were analyzed for eosinophilia to determine if the SP-A peptide could protect from HDM-induced airway eosinophilia by decreasing eosinophil viability. Viability was assessed by Trypan blue exclusion on a cell countess. Peptide sequences: 20-mer PAGRGKEQCVEMYTDGQWND (SEQ ID NO: 8), peptide 1 PAGRGKEQCV (SEQ ID NO: 2), peptide 2 EMYTDGQWND (SEQ ID NO: 3), peptide 3 KEQCVEMYTD (SEQ ID NO: 4).

Figure 8:
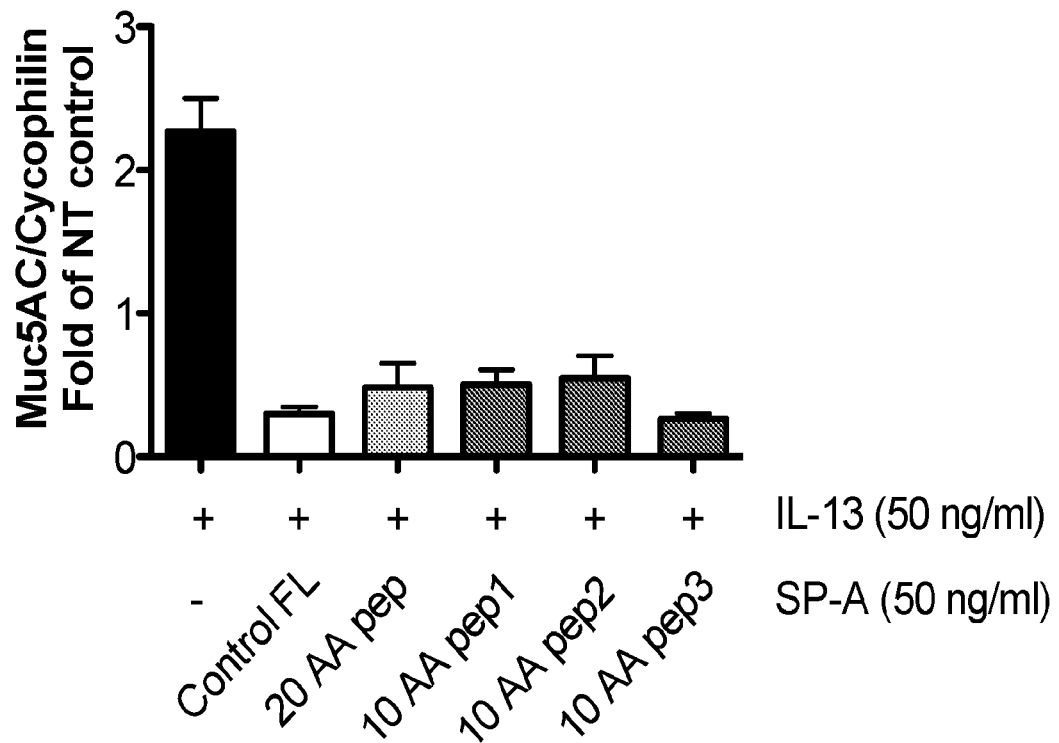
FIG. 8. Shortened 10AA peptides reduce Mucin (Muc5AC RNA) in human primary cells.

Regarding FIG. 8, human bronchial epithelial cells obtained from a well-phenotyped asthmatic were grown at an ALI for two weeks prior to experimentation. For challenge, each of the SP-A test peptides (50 µg/ml) were added to the apical compartment at least 30 minutes prior to IL-13 challenge. Muc5AC was analyzed by RT-PCR from cell lysates and analyzed as a fold over the control samples. Peptide sequences: 20-mer PAGRGKEQCVEMYTDGQWND (SEQ ID NO: 8), peptide 1 PAGRGKEQCV (SEQ ID NO: 2), peptide 2 EMYTDGQWND (SEQ ID NO: 3), peptide 3 KEQCVEMYTD (SEQ ID NO: 4) FL=full length oligomeric SP-A that is extracted from lavage of alveolar proteinosis individuals.

Figure 9:
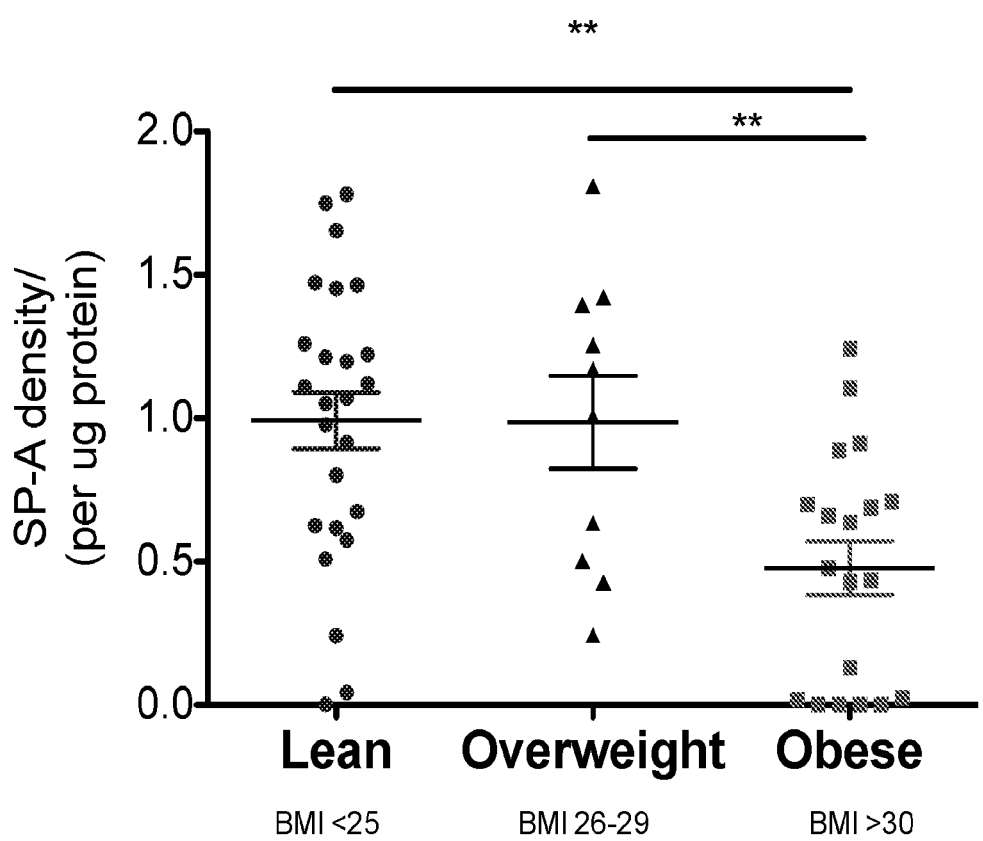
FIG. 9. SP-A is significantly decreased in obesity-potentially a target group for SP-A peptide therapy.

Regarding FIG. 9, SP-A expression was analyzed from the bronchoalveolar lavage of lean, overweight and obese individuals with and without asthma by Western blot.

FIGS. 5-9 show that SP-A223Q humanized mice have less mucus than the 223K mice in an allergic model (Ova model; FIG. 2A), that SP-A223Q humanized mice have less mucus than the 223K mice in an allergic model (HDM (house dust mite) model; FIG. 5), that shortened 10AA peptides reduce mucin production in mouse HDM model (FIG. 6), that shortened 10AA peptides reduce eosinophilia in mouse HDM model (FIG. 7), that shortened 10AA peptides reduce Mucin (Muc5AC RNA) in human primary cells (FIG. 8), and that SP-A is significantly decreased in obesity (FIG. 9).

Example 2

This example describes the use of an HDM sensitization and challenge model in 10-12 adult primates that have been selected by pre-screening for baseline sensitivity to methacholine challenge to test SP-A therapeutic peptide in a crossover study design.

First, HDM allergen is administered to all 10 primates by subcutaneous injection biweekly for 10 weeks, at which time animals are tested for HDM skin reactivity. Next, HDM mask exposure is performed biweekly for a total of 8 weeks. After this HDM challenge period, airway hyperresponsiveness is assessed in all 12 primates and lavage fluid and biopsy specimens are collected for analysis.

After the first round of analysis, in which the level of response each primate has to the HDM model is assessed, the 10 primates are divided into two test groups in a randomized, double-blind crossover design: group 1 (n=6) receive the SP-A peptide followed by washout, then placebo; group 2 (n=6) receive placebo first, followed by washout and then SP-A peptide. SP-A peptide and placebo are given biweekly via intranasal administration for four weeks, while primates are still receiving HDM mask treatments bi-weekly. The dosing of SP-A and placebo is approximately 24 hrs after the HDM mask exposure.

At the end of the first study period at 4 weeks, primates are analyzed for airway hyperresponsiveness. Bronchoscopy is performed for lavage fluid and endobronchial biopsy.

After a four week washout, primates are again be challenged with HDM mask treatments bi-weekly during study period 2. Group 1 (n=6) receive placebo and group 2 (n=6) receive SP-A peptide biweekly following HDM mask treatment for 4 weeks as described above.

After completion of study period 2, all primates are analyzed for airway hyperresponsiveness and bronchoscopy are performed for lavage fluid and endobronchial biopsy.

Statistical Analysis: Primary outcome variables include the airways hyperresponsiveness, lavage and tissue eosinophilia and tissue mucin production. These variables are analyzed by using a two-period crossover analysis of variance model. Carryover effects are tested at the 10% alpha level, whereas period and treatment effects are tested at the 5% alpha level. Data is expressed as means±SEM.

It is anticipated that the SP-A peptide are able to alleviate phenotypes associated with asthma in the HDM allergic model in primates. Thus far, it was shown that one dose of peptide in mice 24 hrs after the last HDM challenge (which is the peak of inflammation) is able to significantly reduce mucin production and eosinophilia in the lavage compartment and in the lung tissue. It is anticipated that giving peptides biweekly over the course of 4 weeks significantly reduces eosinophilia and mucin production as compared to placebo.

Example 3

Figure 10:
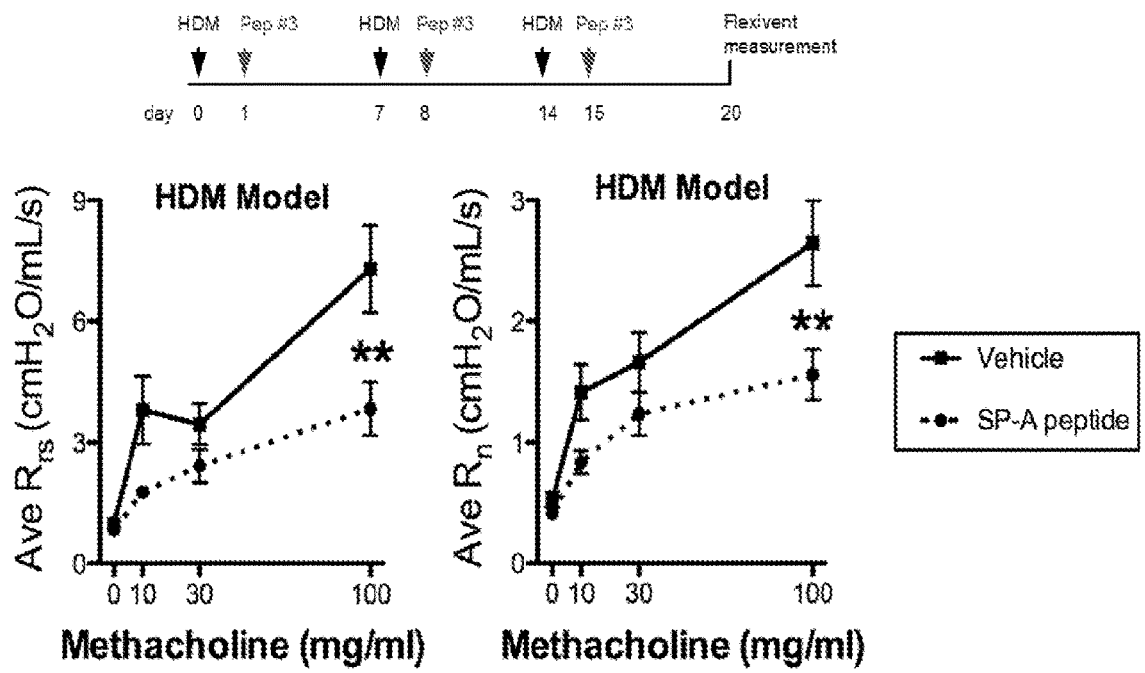
FIG. 10. SP-A peptide protects against AHR in HDM (house dust mite) model.

This example demonstrates that SP-A peptide protects against AHR in HDM (house dust mite) model. As shown in FIG. 10, WT C57BL/6 mice were sensitized and challenged in the HDM model according to standard methods (arrow). Twenty-four hours after each challenge, mice received either scrambled vehicle or a 10-mer SP-A peptide (KEQCVEMYTD (SEQ ID NO: 4)) (arrow) that encompassed the active site containing 223Q (at a physiologic dose of 25 mg/mouse delivered in 40 ml of sterile saline) by oropharyngeal instillation. Pulmonary function tests were conducted 3-5 days post HDM challenge to determine if the SP-A peptide could protect from methacholine-induced airway hyper-responsiveness (AHR). Mice that received the SP-A peptide after HDM challenge had attenuated: overall resistance (Rrs) and central airways resistance (Rn) as compared to HDM challenged mice that received vehicle treatment. Similar protective effects were observed on days 3 and 5 after SP-A peptide treatment.

Example 4

Figure 11:
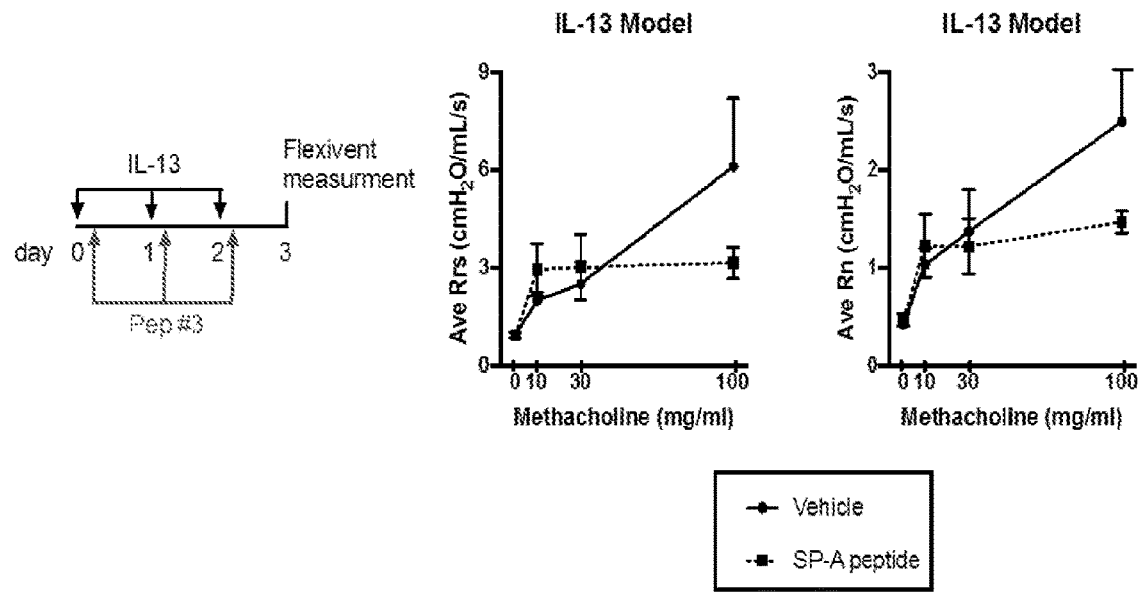
FIG. 11. SP-A peptide protects against airway hyper-responsiveness (AHR) in IL-13 model.

This example demonstrates that SP-A peptide protects against airway hyper-responsiveness (AHR) in IL-13 model. WT C57BL/6 mice were challenged with 3.9 ug of IL-13 (arrow) once a day for 3 consecutive days via oropharyngeal instillation. As shown in FIG. 11, Two hours after each challenge, mice received either scrambled vehicle or a 10-mer SP-A peptide (KEQCVEMYTD (SEQ ID NO: 4)) (arrow) that encompassed the active site containing 223Q (at a physiologic dose of 25 mg/mouse delivered in 40 ml of sterile saline) by oropharyngeal instillation. Pulmonary function tests were conducted 24 hours post IL-13 challenge to determine if the SP-A peptide could protect from methacholine-induced airway hyper-responsiveness (AHR). Mice that received the SP-A peptide after HDM challenge had attenuated: overall resistance (Rrs) and central airways resistance (Rn) as compared to HDM challenged mice that received vehicle treatment.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method, comprising: delivering a composition comprising a peptide consisting of KEQCVEMYTD (SEQ ID NO: 4) to a lung cell in a subject, wherein said delivering results in one or more of enhancing SP-A activity in the cell, and treating asthma in the subject.

2. The method of claim 1, wherein said composition reduces mucin production and/or reduces eosinophilia in said cell.

3. The method of claim 1, wherein said subject is obese.

4. The method of claim 1, wherein said peptide binds to a receptor selected from the group consisting of Fc CD16/32, Sirp-alpha, toll-like receptor 2 (TLR-2) and epidermal growth factor receptor (EGFR).

* * * * *

SEQUENCE LISTING

```
<160> NUMBER OF SEQ ID NOS: 8

<210> SEQ ID NO 1
<211> LENGTH: 248
<212> TYPE: PRT
<213> ORGANISM: Homo sapiens

<400> SEQUENCE: 1

Met Trp Leu Cys Pro Leu Ala Leu Asn Leu Ile Leu Met Ala Ala Ser
1               5                   10                  15

Gly Ala Ala Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45

Gly Val Lys Gly Asp Pro Gly Pro Pro Gly Pro Met Gly Pro Pro Gly
    50                  55                  60

Glu Thr Pro Cys Pro Pro Gly Asn Asn Gly Leu Pro Gly Ala Pro Gly
65                  70                  75                  80

Val Pro Gly Glu Arg Gly Glu Lys Gly Glu Ala Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
    130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 2
<211> LENGTH: 10
<212> TYPE: PRT
<213> ORGANISM: Homo sapiens
```

```
<400> SEQUENCE: 2

Pro Ala Gly Arg Gly Lys Glu Gln Cys Val
1               5                   10

<210> SEQ ID NO 3
<211> LENGTH: 10
<212> TYPE: PRT
<213> ORGANISM: Homo sapiens

<400> SEQUENCE: 3

Glu Met Tyr Thr Asp Gly Gln Trp Asn Asp
1               5                   10

<210> SEQ ID NO 4
<211> LENGTH: 10
<212> TYPE: PRT
<213> ORGANISM: Homo sapiens

<400> SEQUENCE: 4

Lys Glu Gln Cys Val Glu Met Tyr Thr Asp
1               5                   10

<210> SEQ ID NO 5
<211> LENGTH: 10
<212> TYPE: PRT
<213> ORGANISM: Homo sapiens

<400> SEQUENCE: 5

Pro Ala Gly Arg Gly Lys Glu Lys Cys Val
1               5                   10

<210> SEQ ID NO 6
<211> LENGTH: 10
<212> TYPE: PRT
<213> ORGANISM: Homo sapiens

<400> SEQUENCE: 6

Lys Glu Lys Cys Val Glu Met Tyr Thr Asp
1               5                   10

<210> SEQ ID NO 7
<211> LENGTH: 20
<212> TYPE: PRT
<213> ORGANISM: Homo sapiens

<400> SEQUENCE: 7

Pro Ala Gly Arg Gly Lys Glu Lys Cys Val Glu Met Tyr Thr Asp Gly
1               5                   10                  15

Gln Trp Asn Asp
            20

<210> SEQ ID NO 8
<211> LENGTH: 20
<212> TYPE: PRT
<213> ORGANISM: Homo sapiens

<400> SEQUENCE: 8

Pro Ala Gly Arg Gly Lys Glu Gln Cys Val Glu Met Tyr Thr Asp Gly
1               5                   10                  15

Gln Trp Asn Asp
            20
```